United States Patent
Yang

(10) Patent No.: US 10,493,029 B2
(45) Date of Patent: Dec. 3, 2019

(54) ZIYUGLYCOSIDE II POLYMER MICELLE AND PREPARATIVE METHODS THEREOF

(71) Applicant: SICHUAN INLU WEITE PHARMACEUTICAL TECHNOLOGY CO., LTD., Chengdu, Sichuan (CN)

(72) Inventor: Shilin Yang, Beijing (CN)

(73) Assignee: SICHUAN INLU WEITE PHARMACEUTICAL TECHNOLOGY CO., LTD., Chengdu, Sichuan (CN)

( * ) Notice: Subject to any disclaimer, the term of this patent is extended or adjusted under 35 U.S.C. 154(b) by 0 days.

(21) Appl. No.: 16/093,118

(22) PCT Filed: Nov. 7, 2016

(86) PCT No.: PCT/CN2016/104876
§ 371 (c)(1),
(2) Date: Oct. 11, 2018

(87) PCT Pub. No.: WO2017/177668
PCT Pub. Date: Oct. 19, 2017

(65) Prior Publication Data
US 2019/0307683 A1    Oct. 10, 2019

(30) Foreign Application Priority Data
Apr. 11, 2016  (CN) .......................... 2016 1 0221855

(51) Int. Cl.
*A61K 9/107* (2006.01)
*A61P 37/04* (2006.01)
*A61K 31/704* (2006.01)
*A61K 47/34* (2017.01)

(52) U.S. Cl.
CPC .......... *A61K 9/1075* (2013.01); *A61K 31/704* (2013.01); *A61K 47/34* (2013.01); *A61P 37/04* (2018.01)

(58) Field of Classification Search
None
See application file for complete search history.

(56) References Cited

FOREIGN PATENT DOCUMENTS

| CN | 1593436 A | 3/2005 |
|---|---|---|
| CN | 101119740 B | 2/2012 |
| CN | 105147804 A | 12/2015 |

*Primary Examiner* — Layla D Berry
(74) *Attorney, Agent, or Firm* — Novick, Kim & Lee, PLLC; Allen Xue

(57) ABSTRACT

The present invention discloses a ziyuglycoside II polymer micelle, and it is prepared by following raw/auxiliary materials at predetermined weight ratio: 20 parts of ziyuglycoside II and 100-5000 parts of mPEG-PLA-Phe(Boc). Quality evaluation test indicates that only using mPEG-PLA-Phe(Boc) according to the present invention as carrier materials, the quality of ziyuglycoside II polymer micelle prepared is the best, but using other additional materials can lead to the lowered preparation quality. In the pharmacodynamic experiment, compared with the model group, the ziyuglycoside II micelle of the present invention can significantly increase the amounts of WBC, RBC, PLT, NEUT, and HGB in peripheral blood, and the efficacy is obviously better than the original drug ziyuglycoside II, indicating the ziyuglycoside II polymer micelle of the present invention has a better treatment and/or prevention effects on bone marrow suppression, and can improve the bioavailability of insoluble drug ziyuglycoside II.

9 Claims, No Drawings

ZIYUGLYCOSIDE II POLYMER MICELLE AND PREPARATIVE METHODS THEREOF

TECHNICAL FIELD

The present invention relates to a ziyuglycoside II polymer micelle and preparative methods thereof, belonging to pharmaceutical field.

BACKGROUND ART

Bone marrow suppression is a common hematopoietic system disease seen in clinical practice, and many factors such as radiation damage caused by radiation therapy and/or chemotherapy of neoplastic diseases in various systems as well as ionizing radiation, viral hepatitis, micro virus infection or drugs and the like can result in bone marrow suppression. Bone marrow suppression is mainly represented by injuries of bone marrow microenvironment, hematopoietic stem cells, hematopoietic cell growth factors, etc, together with inhibition of cells in one system, two systems and three systems of granulocytic system, erythrocytic system, and megakaryocytic system; amongst, agranulocytosis can cause severe infections, obvious reduction of erythrocytes can cause severe anemia, and obvious decrease of platelets can cause serious hemorrhage and even lead to death. Because marrow suppression seriously threatens lives and health of patients, especially producing adverse effects on neoplastic patients receiving chemoradiation, currently, many research groups are engaged in searching for potent drugs to prevent and treat bone marrow suppression.

Ziyuglycoside II, with chemical name 3-O-α-L-arabinosyl-19α-hydroxyurs-12-en-28-oic acid (ziyuglycoside II), is an active constituent extracted from roots of *Sanguisorba officinalis* L. or *S. officinalis* L. var. *longifolia* (Bertol.) Yu et Li, plants of *Sanguisorba* genus (Rosaceae). CN101119740A has disclosed the use of ziyuglycoside II in preparation of drugs elevating erythrocytes and hemoglobin. However, solubility of ziyuglycoside II in water is low, and gastrointestina absorption rate after oral administration is low, that lead to low bioavailability of this drug taken orally and limit the application in clinical.

Polymer micelle, as a pharmaceutically acceptable carrier, can increase dissolution of insoluble drugs, and has characteristics of stable structure, good tissue permeability, long in vivo retention time, and making drugs effectively reach target point, etc, thus it is an excellent carrier for insoluble drugs. At present, a great variety of carrier materials are used for preparation of polymer micelles, and amphiphilic block copolymers are often utilized. Hydrophilic segment can be selected from polyethylene glycol, polyoxyethylene, povidone, chitosan, etc., while hydrophobic segment materials mainly include polypropylene, polystyrene, polyamino acid, polylactic acid, spermine or short chain phosphatides, etc. Choosing suitable polymer materials according to physicochemical properties of principal drug, thus preparing micelles and obtaining preparations with quality meeting requirements, and allowing that drugs can be effectively released and produce effect in organism, is one of major problems for designing polymer micelles.

Consequently, there is an urgent need for developing a ziyuglycoside II polymer micelle with better preparation quality and definite efficacy, that can be used for treatment and/or prevention of bone marrow suppression.

CONTENT OF THE INVENTION

An object of the present invention is intended to provide a ziyuglycoside II polymer micelle and preparative methods thereof.

The present invention provides a polymer micelle, and it is prepared by following raw/auxiliary materials at predetermined weight ratio: 20 parts of ziyuglycoside II and 100-5000 parts of mPEG-PLA-Phe(Boc).

Further, it is prepared by following raw/auxiliary materials at predetermined weight ratio: 20 parts of ziyuglycoside II and 100-5000 parts of mPEG-PLA-Phe(Boc).

Preferably, it is prepared by following raw/auxiliary materials at predetermined weight ratio: 20 parts of ziyuglycoside II and 400-5000 parts of mPEG-PLA-Phe(Boc).

Further preferably, it is prepared by following raw/auxiliary materials at predetermined weight ratio: 20 parts of ziyuglycoside II and 4000 parts of mPEG-PLA-Phe(Boc).

Wherein, the polymer micelle further contains 0-5 parts of sugar, in which said sugar is selected from one or more among glucose, sucrose, trehalose, fructose, mannitol or lactose.

Wherein, the number average molecular weight of mPEG in mPEG-PLA-Phe(Boc) is 1000-5000, and the number average molecular weight of PLA in mPEG-PLA-Phe(Boc) is 1000-50000.

Further, the number average molecular weight of mPEG in mPEG-PLA-Phe(Boc) is 2000, and the number average molecular weight of PLA in mPEG-PLA-Phe(Boc) is 4000.

The present invention provides a method for preparing the polymer micelle, including the following steps: various weight ratios of ziyuglycoside II and mPEG-PLA-Phe(Boc) are dissolved in 12-125 times volume of ethanol, and then ethanol is evaporated to obtain the polymer micelle.

Further, the preparative method further includes following steps: 0-5 parts of sugar, together with the polymer micelle, is dissolved in water at the same time, allowing the concentration of ziyuglycoside II to be 0.01 mg/mL-20 mg/mL, and then filtered with 0.22 μm micropore film, followed by sterilizing and freeze-drying, to obtain lyophilized powder of polymer micelle.

The present invention provides the uses of polymer micelle in preparation of drugs for treatment and/or prophylaxis of bone marrow suppression.

Further, said drugs are those used for treatment and/or prevention of bone marrow suppression induced by chemical substances.

More further, said drugs are those increasing numbers of one or more of white blood cells (WBC), neutrophilic granulocytes (NEUT), red blood cells (RBC), platelets (PLT) or hemoglobin (HGB) in peripheral blood.

The present invention provides a method for treatment and/or prophylaxis of bone marrow suppression, and it uses the polymer micelle.

The present invention provides a ziyuglycoside II polymer micelle and a preparative method thereof. Quality evaluation test indicates that only using mPEG-PLA-Phe (Boc) according to the present invention as carrier materials, the quality of ziyuglycoside II polymer micelle prepared is the best, but using other additional materials can lead to the lowered preparation quality. In pharmacodynamic experiment, compared with the model group, the ziyuglycoside II micelle of the present invention can significantly increase the amounts of WBC, RBC, PLT, NEUT, and HGB in peripheral blood, and the efficacy is obviously better than the original drug ziyuglycoside II, indicating the ziyuglycoside II polymer micelle of the present invention has a better treatment and/or prevention effects on bone marrow suppression, and can improve the bioavailability of insoluble drug ziyuglycoside II.

Obviously, based on above contents of the present invention, without departing from above basic technical spirit of the present invention, various additional modifications, alternations or changes can also be made by common technical knowledge and commonly-used means in the field.

Hereinafter, the above content of present invention can further be illustrated in detail, combined with specific examples. But it should not be understood that above subject scope of the present invention is only limited to the following examples. The techniques, realizable based on above contents, should all be within the scope of the present invention.

EXAMPLES

Raw materials and equipments used in specific examples of the present invention are all known products, and can be obtained by buying commercially available products.

Example 1 Preparation of Polymer Micelles According to the Present Invention 20 mg ziyuglycoside II and 100 mg mPEG1000-PLA1000-Phe(Boc) were dissolved in 15 ml ethanol, and the solvent was removed by rotary evaporation at 55° C.

50 ml injectable sugar water (containing 5 mg glucose) was added to dissolve drug membrane, and the obtained micelle solution was filtered by 0.22 μm sterile film and freeze-dried, to get lyophilized powder of ziyuglycoside II micelle.

Example 2 Preparation of Polymer Micelles According to the Present Invention 20 mg ziyuglycoside II and 400 mg mPEG2000-PLA4000-Phe(Boc) were dissolved in 15 ml ethanol, and the solvent was removed by rotary evaporation at 55° C.

50 ml injectable sugar water (containing 5 mg glucose) was added to dissolve drug membrane, and the obtained micelle solution was filtered by 0.22 μm sterile film and freeze-dried, to get lyophilized powder of ziyuglycoside II micelle.

Resolubility of above lyophilized powder of ziyuglycoside II micelle in solvents was good, and there are few size distribution changes after redissolution. The content of principal drug was 0.4 mg/mL, with an entrapment rate of >99%, a particle size of <100 nm, and PDI of <0.3.

Example 3 Preparation of Polymer Micelles According to the Present Invention 20 mg ziyuglycoside II and 2000 mg mPEG5000-PLA3000-Phe(Boc) were dissolved in 50 ml ethanol, and the solvent was removed by rotary evaporation at 55° C.

50 ml injectable sugar water (containing 5 mg trehalose) was added to dissolve drug membrane, and the obtained micelle solution was filtered by 0.22 μm sterile film and freeze-dried, to get lyophilized powder of ziyuglycoside II micelle.

Example 4 Preparation of Polymer Micelles According to the Present Invention 20 mg ziyuglycoside II and 4000 mg mPEG2000-PLA5000-Phe(Boc) were dissolved in 50 ml ethanol, and the solvent was removed by rotary evaporation at 55° C.

50 ml injectable sugar water (containing 5 g fructose) was added to dissolve drug membrane, and the obtained micelle solution was filtered by 0.22 μm sterile film and freeze-dried, to get lyophilized powder of ziyuglycoside II micelle.

Hereinafter, beneficial effects of the present invention were proved by following examples.

Assaying:

Apparatus: High performance liquid chromatograph Waters e2695

Chromatographic condition: chromatographic column: octadecylselyl bonded silica gel (4.6×250 mm, 5 μm)

Detection wavelength: 203 nm

Mobile phase: methanol: 0.1% formic acid=80:20

Flow rate: 1 mL/min

Column temperature: 25° C.

Sample size: 20 μL

Sample preparation: The solution of ziyuglycoside II micelle was diluted suitable multiples with MeOH, and injected to high performance liquid chromatograph to measure the particle size and distribution.

Determination of Particle Size and Distribution:

Apparatus: Malvern ZS90

Sample preparation: The solution of ziyuglycoside II micelle was diluted suitable multiples with ultrapure water, and injected to particle size analyzer to measure the particle size and distribution.

Example 1 Quality Evaluation of Polymer Micelles Prepared Using Different Carrier Materials At the early stage of the present study, according to properties of ziyuglycoside II, various amphiphilic block copolymers constituted by hydrophilic materials and hydrophobic materials were investigated, and five materials providing better quality of polymer micelles were listed in the following.

1. mPEG-PLA-Phe(Boc): tert-butoxyphenylalanine-terminated methoxypolyethylene glycol-polylactic acid block copolymer, its hydrophilic chain is mPEG with a number average molecular weight of 1000-5000, and its lipophilic chain is PLA with a number average molecular weight of 1000-5000, and its structure is shown as formula I:

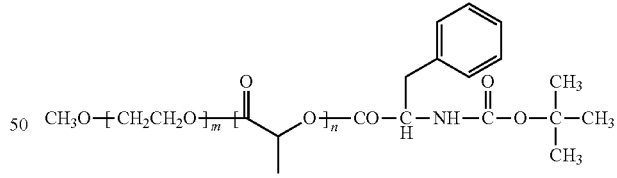

Formula I

For T the synthetic method of high molecular polymer, seeing references: [1] Chen xue-dong, Yang shi-lin, Feng yu-lin, Liu ke, et al, Preparation and characterization of arctigenin mPEG-PDLLA polymer micelles [J]. Medicine, 2015, 18(8): 153; [2] Chen xue-dong, Preparation and evaluation of a new carrier docetaxel mPEG-PDLLA-Phe (Boc) micelles, Master degree thesis of Jiangxi University of Traditional Chinese Medicine, 2016.6.

2. mPEG-PLA: methoxypolyethylene glycol-polylactic acid block copolymer, its hydrophilic chain is mPEG with a number average molecular weight of 1000-5000, and its lipophilic chain is PLA with a number average molecular weight of 1000-5000, and its structure is shown as formula II:

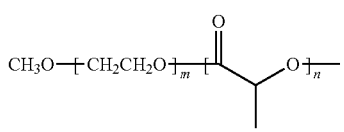

Formula II

For the synthetic method of high molecular polymer, seeing above references.

3. Poloxamer F68, i.e. Poloxamer, is a polyoxyethylene polyoxypropylene block copolymer.
4. Solutol HS15 is a polyethylene glycol-12-hydroxystearate.
5. Polyoxyethylene castor oil EL35.

Poloxamer F68, Solutol HS15, and polyoxyethylene castor oil EL35 were all purchased from BASF company, Germany.

Experimental Method 1. 20 mg Ziyuglycoside II and 400 mg different high polymer materials mPEG2000-PLA4000-Phe(Boc), mPEG2000-PLA4000, Poloxamer F68, Solutol HS15, and polyoxyethylene castor oil EL35 were dissolved in 15 ml EtOH, respectively, and after removal of solvents by rotary evaporation at 55° C., 50 ml water for injection was added to dissolve drug membrane. After the obtained micelle solution was filtered by 0.22 µm sterile film, the content of ziyuglycoside II in micelles and its particle size distribution were determined, and results were shown in Table 1.

TABLE 1

Quality evaluation of polymer micelles prepared using different carrier materials

| Carrier materials | Content of drug (mg/mL) | Mean diameter (nm) | PDI |
|---|---|---|---|
| mPEG-PLA-Phe(Boc) | 0.391 | 87 | 0.16 |
| mPEG-PLA | 0.111 | 157 | 0.31 |
| Poloxamer F68 | 0.088 | 43 | 0.19 |
| Solutol HS15 | 0.135 | 38 | 0.13 |
| polyoxyethylene castor oil EL35 | 0.154 | 35 | 0.09 |

Experimental results: the content of ziyuglycoside II was highest (up to 0.391 mg/mL) in polymer micelles prepared by carrier materials mPEG-PLA-Phe(Boc) according to the present invention, the mean diameter was smaller (87 nm), and the dispersion index (PDI) was only 0.16, indicating the particle size of obtained micelles was very uniform. Two additional materials mPEG-PLA and Poloxamer F68 can cause the content of drug or the uniformity of particle diameter to obviously reduce, moreover, the mean diameter of micelles obtained using mPEG-PLA was bigger and unsuitable for injection. Using Solutol HS15 and polyoxyethylene castor oil EL35 also had the problems that the content of drug decreased.

Above experimental results indicated: only when mPEG-PLA-Phe(Boc) of the present invention was used as carrier materials, the quality of ziyuglycoside II polymer micelles prepared was the best, and using other materials can result in the decrease of preparation quality.

2. 20 mg Ziyuglycoside II and 400 mg mPEG-PLA-Phe(Boc) with different number average molecular weight were dissolved in 15 ml EtOH, respectively, and after removal of solvents by rotary evaporation at 55° C., 50 ml water for injection was added to dissolve drug membrane. After the obtained micelle solution was filtered by 0.22 µm sterile film, the content of ziyuglycoside II in micelles and its particle size distribution were determined, and results were shown in Table 2.

TABLE 2

Quality evaluation of polymer micelles prepared using mPEG-PLA-Phe(Boc) with different molecular weight

| Number average molecular weight of carrier materials | Content of drug (mg/mL) | Mean diameter (nm) | PDI |
|---|---|---|---|
| mPEG1000-PLA1000-Phe(Boc) | 0.091 | 187 | 0.38 |
| mPEG2000-PLA1000-Phe(Boc) | 0.211 | 557 | 0.26 |
| mPEG5000-PLA3000-Phe(Boc) | 0.389 | 489 | 0.21 |
| mPEG2000-PLA4000-Phe(Boc) | 0.391 | 87 | 0.16 |
| mPEG2000-PLA5000-Phe(Boc) | 0.401 | 574 | 0.33 |

Experimental results: when only using mPEG-PLA-Phe(Boc) with a number average molecular weight in the range of the present invention, the ziyuglycoside II polymer micelles can be prepared; amongst, the content of ziyuglycoside II was highest (up to 0.391 mg/mL) in polymer micelles prepared by mPEG2000-PLA4000-Phe(Boc), the mean diameter was smaller (87 nm), and the dispersion index (PDI) was only 0.16, indicating the quality of obtained micelles was the best.

Example 2 Quality Evaluation of Polymer Micelles Prepared According to the Usage Amount of Different Carrier Materials Ziyuglycoside II and MPEG2000-PLA4000-Phe(Boc) were weighed and taken out at a mass ratio of 1:3-1:250 (the weight of ziyuglycoside II was fixed to 20 mg, and the weight of MPEG-PLA-Phe(Boc) can be changed as the ratio), and were dissolved in 50 ml EtOH, respectively. After removal of solvents by rotary evaporation at 55° C., 50 ml water for injection was added to dissolve drug membrane. After the obtained micelle solution was filtered by 0.22 µm sterile film, the content of ziyuglycoside II in micelles and its particle size distribution were measured, and results were shown in Table 3.

TABLE 3

Quality evaluation of polymer micelles prepared according to the usage amount of different carrier materials

| (mass ratio) ziyuglycoside II:mPEG-PLA-Phe(Boc) | Content of drug (mg/mL) | Mean diameter (nm) | PDI |
|---|---|---|---|
| 1:3 | 0.005 | 120 | 0.67 |
| 1:4 | 0.008 | 117 | 0.56 |
| 1:5 | 0.011 | 88 | 0.19 |
| 1:10 | 0.038 | 85 | 0.16 |
| 1:20 | 0.394 | 87 | 0.16 |
| 1:50 | 0.392 | 76 | 0.11 |
| 1:100 | 0.401 | 81 | 0.13 |
| 1:200 | 0.408 | 85 | 0.09 |
| 1:250 | 0.399 | 83 | 0.11 |

Experimental results: when the usage amount of carrier material MPEG-PLA-Phe(Boc) was 5-250 times that of ziyuglycoside II, the quality of obtained polymer micelles was better: the content of drug was not less than 0.01 mg/mL, the mean diameter was below 90 nm, and PDI was all below 0.2; amongst, the usage amount of MPEG-PLA-Phe(Boc) was in the range of 20-250 times that of ziyuglycoside II, and the preparation quality could be further optimized, that was shown by the higher content of drug (the content can reach about 0.4 mg/mL); amongst, when the mass ratio of ziyuglycoside II and mPEG-PLA-Phe(Boc) was 1:200, the quality of micelles was the best: the content of drug was higher, and the size distribution was the most uniform.

Example 3 Pharmacodynamic Experiment of Ziyuglycoside II Polymer Micelles According to the Present Invention 1. Experimental Materials, Reagents, Apparatus Test drugs were ziyuglycoside II micelles and ziyuglycoside II powder.

Tool drug was cyclophosphamide.

Laboratory animals were KM-mice: 18.5-22.5 g.

Laboratory apparatus: Automatic blood counting analyzer; BS-600L electronic balance: specification: 600 g/0.1 g, Shanghai Yousheng Weighing Apparatus Co. Ltd.

2. Statistical Method

Statistical analysis was performed using SPSS 17.0 software. Data were expressed as mean±standard error ($\bar{x}\pm S$), and one-factor analysis of variance was used among groups. For homogeneity of variance, data between groups were compared by LSD test, while for heterogeneity of variance, data between groups were compared by Tamhane's T2 test.

3. Experimental Method 3.1 Grouping of Laboratory Animals and Establishing Model After all animals were adaptively fed for one week, according to the body weight, animals were randomly divided as blank group; model group; ziyuglycoside II micelle sample groups 1-4 (respectively using micelles prepared in examples 1-4), with a dosage of 2.5 mg·kg$^{-1}$, preparation before use; ziyuglycoside II group: powder of ziyuglycoside II raw materials, dissolved in 10% DMSO-normal saline, with a dosage of 2.5 mg·kg$^{-1}$, preparation before use. On the first day of experiment, except for blank group, mice in other groups received cyclophosphamide normal saline solution at a dose of 120 mg·kg$^{-1}$ by peritoneal injection, and mice in blank group received the same volume of normal saline by peritoneal injection.

3.2 Administration

From the first day of experiment, each experimental group was given the corresponding drug as the predetermined dosage and administration mode, and mice in blank group and model group were given a same volume of normal saline by injection into the tail vein, for successive 6 days.

3.3 Sample Collection

On the seventh day of experiment, whole blood was collected from orbit of mice in each experimental group, and placed in 0.5 ml EP tubes containing EDTA anticoagulant agent for test.

3.4 Detection Index and Method

White blood cells (WBC), neutrophilic granulocytes (NEUT), red blood cells (RBC), platelets (PLT), and hemoglobin (HGB) in peripheral blood of mice in each experimental group were counted using automatic blood counting instrument.

4. Experimental Results

TABLE 4

Numbers of WBC, RBC, and PLT in peripheral blood of mice in each experimental group

| Groups | Dosage (mg/kg) | WBC ($\times 10^9$) | RBC ($\times 10^{12}$) | PLT ($\times 10^9$) |
| --- | --- | --- | --- | --- |
| Blank group | — | 6.78 ± 0.15$^{\Delta*}$ | 5.96 ± 0.11$^{\Delta*}$ | 476.16 ± 12.27$^{\Delta*}$ |
| Model group | — | 3.32 ± 0.52 | 3.23 ± 0.41 | 218.33 ± 12.15 |
| Micelle sample 1 | 2.5 | 5.62 ± 0.13$^{\Delta*}$ | 5.42 ± 0.12$^{\Delta*}$ | 431.91 ± 10.21$^{\Delta*}$ |
| Micelle sample 2 | 2.5 | 5.70 ± 0.21$^{\Delta*}$ | 5.38 ± 0.25$^{\Delta*}$ | 439.73 ± 10.31$^{\Delta*}$ |
| Micelle sample 3 | 2.5 | 5.69 ± 0.15$^{\Delta*}$ | 5.35 ± 0.32$^{\Delta*}$ | 437.84 ± 10.26$^{\Delta*}$ |
| Micelle sample 4 | 2.5 | 5.61 ± 0.36$^{\Delta*}$ | 5.39 ± 0.35$^{\Delta*}$ | 435.02 ± 11.21$^{\Delta*}$ |
| Ziyuglycoside II | 2.5 | 3.71 ± 0.13 | 3.54 ± 0.11 | 221.18 ± 6.15 |

Note:
compared with model group,
*P < 0.05,
**P < 0.01;
Note:
compared with ziyuglycoside II group,
$^{\Delta}$P < 0.05,
$^{\Delta\Delta}$P < 0.01.

Experimental results: compared with model group, numbers of WBC, RBC, and PLT in peripheral blood of mice in groups 1-4 of ziyuglycoside II micelle sample according to the present invention significantly increased (P<0.05), while ziyuglycoside II group did not show significant difference; compared with ziyuglycoside II group, numbers of WBC, RBC, and PLT in peripheral blood of mice in groups 1-4 of ziyuglycoside II micelle sample according to the present invention significantly increased (P<0.05).

TABLE 5

Numbers of NEUT and HGB in peripheral blood of mice in each experimental group

| Groups | Dosage (mg/kg) | NEUT ($\times 10^9$) | HGB (g/L) |
| --- | --- | --- | --- |
| Blank group | — | 6.98 ± 0.15$^{\Delta*}$ | 98.59 ± 5.17$^{\Delta*}$ |
| Model group | — | 2.41 ± 0.14$^{\Delta}$ | 43.42 ± 7.26$^{\Delta}$ |
| Micelle sample 1 | 2.5 | 6.12 ± 0.12$^{\Delta*}$ | 89.53 ± 5.10$^{\Delta*}$ |
| Micelle sample 2 | 2.5 | 6.22 ± 0.32$^{\Delta*}$ | 88.61 ± 6.17$^{\Delta*}$ |
| Micelle sample 3 | 2.5 | 5.99 ± 0.14$^{\Delta*}$ | 88.95 ± 9.20$^{\Delta*}$ |
| Micelle sample 4 | 2.5 | 5.99 ± 0.37$^{\Delta*}$ | 89.47 ± 3.58$^{\Delta*}$ |
| Ziyuglycoside II | 2.5 | 2.47 ± 0.55 | 44.65 ± 7.27 |

Note:
compared with model group,
*P < 0.05,
**P < 0.01;
Note:
compared with ziyuglycoside II group,
$^{\Delta}$P < 0.05,
$^{\Delta\Delta}$P < 0.01.

Experimental results: compared with model group, numbers of NEUT and HGB in peripheral blood of mice in groups 1-4 of ziyuglycoside II micelle sample according to the present invention significantly increased (P<0.05), while ziyuglycoside II group did not show significant difference; compared with ziyuglycoside II group, numbers of NEUT and HGB in peripheral blood of mice in groups 1-4 of ziyuglycoside II micelle sample according to the present invention significantly increased (P<0.05).

Above experimental results indicated: the ziyuglycoside II polymer micelle of the present invention has a better treatment and/or prevention effects on bone marrow suppression, and the efficacy was obviously better than direct administration of ziyuglycoside II raw materials.

The invention claimed is:

1. A polymer micelle, comprising 20 weight parts of ziyuglycoside II and 100-5000 weight parts of mPEG-PLA-Phe(Boc).

2. The polymer micelle according to claim 1, comprising 20 weight parts of ziyuglycoside II and 400-5000 weight parts of mPEG-PLA-Phe(Boc).

3. The polymer micelle according to claim 2, comprising 20 weight parts of ziyuglycoside II and 4000 weight parts of mPEG-PLA-Phe(Boc).

4. The polymer micelle according to claim 1, further comprising less than 5 weight parts of sugar, wherein the sugar is selected from the group consisting of glucose, sucrose, trehalose, fructose, mannitol, lactose, and mixtures thereof.

5. The polymer micelle according to claim 1, wherein a number average molecular weight of mPEG in mPEG-PLA-Phe(Boc) is 1000-5000, and a number average molecular weight of PLA in mPEG-PLA-Phe(Boc) is 1000-50000.

6. The polymer micelle according to claim 5, wherein the number average molecular weight of mPEG in mPEG-PLA-Phe(Boc) is 2000, and the number average molecular weight of PLA in mPEG-PLA-Phe(Boc) is 4000.

7. A method for preparing the polymer micelle according to claim 1, comprising: dissolving ziyuglycoside II and mPEG-PLA-Phe(Boc) in ethanol; and evaporating ethanol to obtain the polymer micelle.

8. The method according to claim 7, further comprising: dissolving sugar and the polymer micelle in water to obtain a solution; when a concentration of ziyuglycoside II in the solution is 0.01 mg/mL-20 mg/mL, filtering the solution using a 0.22 µm micropore film; sterilizing and freeze-drying to obtain lyophilized powder of polymer micelle.

9. A method for treatment and/or prophylaxis of bone marrow suppression, comprising administering a pharmaceutically suitable amount of the polymer micelle of claim 1 to a subject in need thereof.

* * * * *